United States Patent [19]

Kaneko

[11] Patent Number: 4,970,142
[45] Date of Patent: Nov. 13, 1990

[54] SILVER HALIDE PHOTOGRAPHIC LIGHT-SENSITIVE MATERIAL CONTAINING CYAN COUPLER

[75] Inventor: Yutaka Kaneko, Hino, Japan
[73] Assignee: Konica Corporation, Tokyo, Japan
[21] Appl. No.: 478,648
[22] Filed: Feb. 12, 1990
[30] Foreign Application Priority Data

Feb. 16, 1989 [JP] Japan .................................. 1-36996
Mar. 4, 1989 [JP] Japan .................................. 1-52293

[51] Int. Cl.$^5$ ................................................. G03C 7/38
[52] U.S. Cl. .................................... 430/558; 430/384; 430/385
[58] Field of Search ..................... 430/558 R, 384, 385

[56] References Cited

U.S. PATENT DOCUMENTS 3,171,740  3/1965  Menzel et al. ....................... 430/558
4,873,183 10/1989  Tachibana et al. .................. 430/558

Primary Examiner—Richard L. Schilling
Attorney, Agent, or Firm—Frishauf, Holtz, Goodman & Woodward

[57] ABSTRACT

A silver halide photographic light-sensitive material is disclosed, which contains a novel color forming coupler so that the fastness of dye image formed therein is improved against heat and light. The color forming coupler is represented by the following Formula I or II;

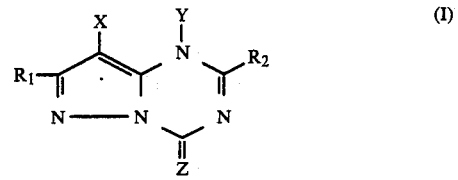

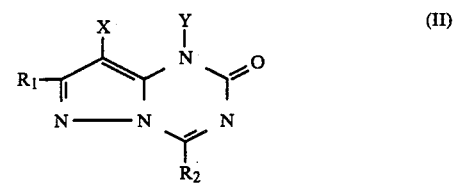

wherein $R_1$, $R_2$ and Y are independently a hydrogen atom or a substituent; Z is an oxygen atom or a sulfur atom, X is a hydrogen atom or substituent capable of split off upon reaction with the oxidation product of a color developing agent.

13 Claims, No Drawings

SILVER HALIDE PHOTOGRAPHIC LIGHT-SENSITIVE MATERIAL CONTAINING CYAN COUPLER

FIELD OF THE INVENTION

This invention relates to a silver halide photographic light-sensitive material containing a novel coupler capable of forming a dye image having an excellent fastness against heat, moisture and light.

BACKGROUND OF THE INVENTION

In an ordinary method for obtaining a color photograph, color images are obtained in the following manner:

A silver halide photographic light-sensitive material, hereinafter referred to as a photographic light-sensitive material, is exposed to light and then color developed, thereby reacting the oxidation product of an aromatic primary amine color developing agent with a dye-forming coupler to produce a dye, so that a color image may be obtained.

In this method, yellow, magent and cyan images are produced for color reproducing by an subtractive color reproducing system.

The photographic couplers for producing the above-mentioned yellow images include, for example, an acylacetoanilide type coupler. Those producing magenta images include, for example, couplers of the pyrazolone type, pyrazolobenzimidazole type, pyrazolotriazole type and indazolone type. Those producing cyan images include, for example, couplers of the phenol type and naphthol type.

The dye images thus obtained are so required as not to be discolored nor faded, even when they are exposed to light for a long time or stored under the high temperature and humidity conditions.

For serving as the couplers for forming cyan dyes, the phenol and naphthol types of couplers have been researched. However, they have still been unable to satisfy the spectral absorption characteristics, moisture resistance, heat resistance and light fastness of cyan dye images thus produced. Accordingly to improve the above-mentioned problems, there have been various proposals including those for the devices of substituents. However, there has been no compound found to solve all the above-mentioned problems.

SUMMARY OF THE INVENTION

It is an object of the invention to provide a photographic light-sensitive material capable of producing a cyan dye image substantially resistive against hue variations caused by heat, moisture and/or light.

The above-described object of the invention can be achieved by a silver halide photographic light-sensitive material containing a coupler represented by the following Formula I or II:

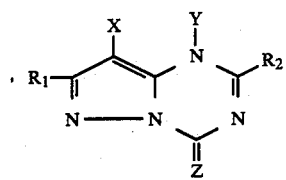

Formula I

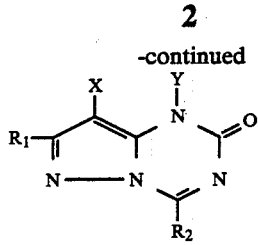

Formula II wherein $R_1$, $R_2$ and Y are each a hydrogen atom or a substituent, X is a hydrogen atom or a substituent which is split off upon reaction with the oxidation product of a color developing agent, and Z is an oxygen atom or a sulfur atom.

DETAILED DESCRIPTION OF THE INVENTION

In the above-given Formulas, $R_1$ and $R_2$ represent each a hydrogen atom or a substituent. The substituents shall not specially be limitative but include, typically, an alkyl group, an aryl qroup, an anilino group, an acylamino group, a by silver halide photographic light-sensitive material comprising a silver halide emulsion lay, in which the light-sensitive sulfonamido group, an alkylthio group, an arylthio group, an alkenyl group, and a cycloalkyl group. Besides the above, they also include, for example, a halogen atom, a cycloalkenyl group, an alkinyl group, a heterocyclic group, a sulfonyl group, a sulfinyl group, a phosphonyl group, an acyl group, a carbamoyl group, a sulfamoyl group, a cyano group, an alkoxy group, a sulfonyloxy group, an aryloxy group, a heterocyclic oxy group, a siloxy group, an acyloxy group, a carbamoyloxy group, an amino group, an alkylamino group, an imido group, a ureido group, a sulfamoylamino group, an alkoxycarbonylamino group, an aryloxycarbonylamino group, an alkoxycarbonyl group, an aryloxycarbonyl group, a heterocyclic thio group, a thioureido group, a carboxy group, a hydroxy group, amercapto group, a nitro group, and a sulfone group, as well as a spiro compound residual group, and a bridged hyrocarbon compound residual group.

Among the substituents represented each by $R_1$ and $R_2$, the alkyl groups should be preferable to have 1 to 32 carbon atoms, and they may be straight-chained or branched.

The aryl groups should be preferable to be a phenyl group.

The acylamino groups include an alkylcarbonylamino group, and an arylcarbonylamino group.

The sulfonamido groups include an alkylsulfonylamino group, and an arylsulfonylamino group.

The alkyl and aryl components of the alkylthio and arylthio groups include an alkyl and aryl groups each represented by $R_1$ and $R_2$.

The alkenyl groups include those having 2 to 32 carbon atoms, and they may be straight-chained or branched.

The cycloalkyl groups include those having 3 to 12 carbon atoms and, preferably, those having 5 to 7 carbon atoms.

The cycloalkenyl groups include those having 3 to 12 carbon atoms and, preferably, those having 5 to 7 carbon atoms.

The sulfonyl groups include an alkylsulfonyl group and an arylsulfonyl group.

The sulfinyl groups include an alkylsulfinyl group and an arylsulfinyl group.

The phosphonyl groups include an alkylphosphonyl group, an alkoxyphosphonyl group, an aryloxyphosphonyl group, and an arylphosphonyl group.

The acyl groups include an alkylcarbonyl group, and an arylcarbonyl group.

The carbamoyl groups include an alkylcarbamoyl group and an arylcarbamoyl group.

The sulfamoyl groups include an alkylsulfamoyl group, and an arylsulfamoyl group.

The acyloxy groups include an alkylcarbonyloxy group and an arylcarbonyloxy group.

The carbamoyloxy groups include an alkylcarbamoyloxy group and an arylcarbamoyloxy group.

The ureido groups include an alkylureido group and arylureido group.

The sulfamoylamino groups include an alkylsulfamoylamino group and an arylsulfamoylamino group.

The heterocyclic groups include, preferably, those having 5 to 7 members and, typically, a 2-furyl group, a 2-thienyl group, a 2-pyrimidinyl group, a 2-benzothiazolyl group, a 1-pyrolyl group, and a 1-tetrazolyl group.

The heterocyclic oxy groups include, preferably, those having a 5 to 7 membered hetero ring and, typically, a 3,4, 5,6-tetrahydropyranyl-2-oxy group, and a 1-phenyltetrazole-5-oxy group.

The heterocyclic thio groups include, preferably, those having 5 to 7 members and, typically, a 2-pyridylthio group, a 2-benzothiazolylthio group, and a 2,4-diphenoxy-1,3,5-triazole-6-thio group.

The siloxy groups include a trimethylsiloxy group, a triethylsiloxy group, and a dimethylbutylsiloxy group.

The imido groups include a succinimido group, a 3-heptadecylsuccinimido group, a phthalimido group, and a glutarimido group.

The spiro compound residual groups include a spiro [3,3]heptane-1-yl group.

The bridged hydrocarbon compound residual groups include a bicyclo[2,2,1]heptane-1-yl group, a tricyclo[3,3,1,1$^{37}$] decane-1-yl group, and a 7,7-dimethylbicyclo[2,2,1]heptane-1-yl group.

The above-given groups may also have a substituent including, for example, a ballast group such as a long-chained hydrocarbon group and a polymer residual group.

The groups each capable of being split off upon reaction with the oxidation product of a color developing agent include, for example, a halogen atom such as a chlorine atom, a bromine atom and a fluorine atom, an alkylene group, an alkoxy group, an aryloxy group, a heterocyclic oxy group, an acyloxy group, a sulfonyloxy group, an alkoxycarbonyloxy group, an aryloxycarbonyl group, an alkyloxalyloxy group, an alkoxyoxalyloxy group, an alkylthio group, an arylthio group, a heterocyclic thio group, an alkyloxythiocarbonylthio group, an acylamino group, a sulfonamido group, a nitrogen-containing heterocyclic group coupling at an N atom thereof to the coupler residue, an alkyloxy carbonylamino group, an aryloxycarbonylamino group, and a carboxyl group. Among the groups represented by the fore going Formulas I and II, the groups represented by the following Formulas Ia and IIa may also be included, respectively.

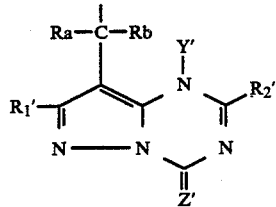

Formula Ia

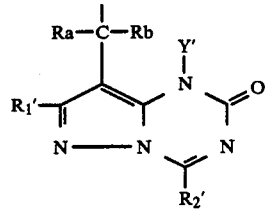

Formula IIa wherein $R_1'$, $R_2'$, $Y'$ and $Z'$ are each synonymous with the foregoing $R_1$, $R_2$, Y and Z, respectively, and Ra and Rb represent each a hydrogen atom, an aryl group, an alkyl group, or a heterocyclic group.

Among the above groups of atoms represented by X, a hydrogen atom and a halogen atom are preferable and a hydrogen atom and a chlorine atom are particularly preferable.

In the foregoing Formula I or II, Y represents a hydrogen atom or a substituent. Among the substituents represented by Y, the preferable ones include, for example, those capable of being split off from the compound of the invention upon reaction of the compound with the oxidized product of a developing agent. The substituents include those capable of being split off under the alkaline conditions, such as those described in Japanese Patent Publication Open to Public Inspection (hereinafter referred to as Japanese Patent O.P.I. Publication) No. 61-228444/1986, and those capable of coupling off upon reaction with the oxidized product of a developing agent, such as those described in Japanese Patent O.P.I. Publication No. 56-133734/1981. Y preferably represents a hydrogen atom. Z preferably represents an oxygen atom in Formula I.

Accordingly, compounds of the invention represented by Formulas 1 and 11 are preferably ones represent by the following Formulas Ib and IIb, respectively.

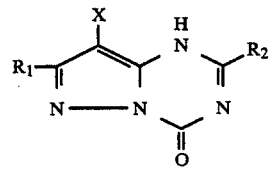

Ib

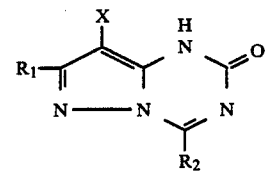

IIb in the above formulas $R_1$, $R_2$ and X are the same as defined in Formulas I and II.

The typical examples of the compounds of the invention will be given below. It is, however, to be understood that the invention shall not be limited thereto.

Compounds represented by Formula I

| No. | R₁ | R₂ | X |
|---|---|---|---|
| I-1 | H | H | H |
| I-2 | —CH₃ | H | H |
| I-3 | —C₁₅H₃₁ | H | Cl |
| I-4 | —C₆H₅ (phenyl) | H | H |
| I-5 | —C₆H₄-CH₃ (p-tolyl) | H | Cl |
| I-6 | —SCH₂—C₆H₄—NHCOCH(C₆H₁₃)— (2,4-di-t-C₅H₁₁)C₆H₃ | H | Cl |
| I-7 | —SO₂—C₆H₄—NHSO₂C₁₁H₂₃ | H | H |
| I-8 | —NH—C₆H₄—OC₁₈H₃₇ | H | Br |
| I-9 | —OC₁₂H₂₅ | H | Cl |

$$\underset{\text{Formula I}}{\begin{array}{c}\text{R}_1-\text{pyrazolotriazinone with R}_2, X\end{array}}$$

-continued

| No. | R₁ | R₂ | X |
|---|---|---|---|
| I-10 | —NHCONH—C₆H₄—C₁₁H₂₃ | H | H |
| I-11 | —CONHC₁₂H₂₅ | H | Cl |
| I-12 | —SO₂N(C₈H₁₇)₂ | H | H |
| I-13 | —COCH₂—C₆H₄—NHCOC₁₃H₂₇ | H | Cl |
| I-14 | H | H | (tetrahydrofuran sugar: CH₂OH, OH, HO) |
| I-15 | —CH₃ | —C₆H₄—OC₁₂H₅ (p-dodecyloxyphenyl) | H |
| I-16 | —CH(CH₃)₂ | —C₆H₄—NHSO₂C₂₁H₂₅ (o-) | Cl |
| I-17 | —C₆H₂(C₄H₉(t))(OCH₂O)—NHCOCH(C₁₂H₂₅)— | H | Cl |
| I-18 | —SO₂CH₂—C₆H₄—OC₁₂H₂₅ | 5-methylfuran-2-yl | H |
| I-19 | —C₁₂H₂₅ | —NHSO₂C₁₂H₂₅ | H |
| I-20 | —COOC₁₈H₃₇ | H | Cl |

-continued

| No. | R₁ | R₂ | X |
|---|---|---|---|
| I-21 | (2-methylfuran-5-yl) | Cl | Cl |
| I-22 | —SCH₃ | —NHCOC₁₃H₂₇ | H |
| I-23 | —NHSO₂—C₆H₄—OC₁₂H₂₅ | phenyl | H |
| I-24 | —NHSO₂—C₆H₄—Cl | Cl | H |
| I-25 | —C(CH₃)₂—CH₂SO₂C₁₈H₃₇ | (6-methylpyridin-2-yl) | Cl |
| I-26 | —C₁₆H₃₃ | (2-methylphenyl)-OCH₃ | —OCH₃ |
| I-27 | —NHC₆H₅ | Br | H |
| I-28 | (3-NHCOC₁₁H₂₃-phenyl) | phenyl | H |
| I-29 | —SO₂NH—C₆H₄—OC₁₁H₂₃ | —NHCOCH₃ | H |

-continued

| No. | R₁ | R₂ | X |
|---|---|---|---|
| I-30 | −CO−C₆H₄−C₁₁H₂₃ (para) | −C₆H₄−CH₃ (para) | H |
| I-31 | −SO₂N(C₃H₇)₂ | −NHSO₂−C₆H₃(OC₄H₉)(C₈H₁₇) | H |
| I-32 | −SO₂NHC₁₂H₂₅ | −(CH₂)₃O−C₆H₄−C₁₅H₃₁ | Cl |
| I-33 | −COOCH₃ | −C₆H₄−NHSO₂−C₆H₄−OH | −N(pyrazol-1-yl) |
| I-34 | −COCH₃ | −C₆H₃(C₅H₁₁(t))−NHCOCHO−C₁₁H₂₃ (with C₅H₁₁(t)) | H |
| I-35 | −CH₂−C₆H₄−NHCOC₁₈H₃₇ | −C₆H₄−Cl (ortho) CH₃ | Cl |
| I-36 | −CH₃ | −NHSO₂−C₆H₃(OC₄H₉)(C₈H₁₇) | −N=N−C₆H₄−COOC₂H₅ |

-continued
| No. | $R_1$ | $R_2$ | X |
|---|---|---|---|
| I-37 | 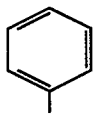 | 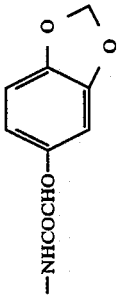 | 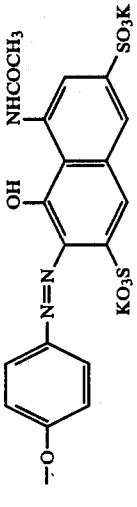 |
| I-38 | H |  | 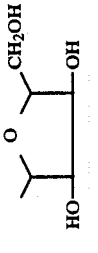 |
| I-39 | —$CH_3$ | H | Cl |
| I-40 |  | 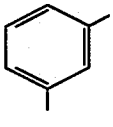 | H |
| I-41 | —$C(CH_3)_3$ |  | Cl |
| I-42 | —$C_{16}H_{33}$ | 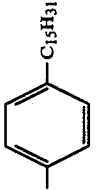 | H |

-continued

| No. | $R_1$ | $R_2$ | X |
|---|---|---|---|
| I-43 | —SO$_2$CH$_2$C$_6$H$_5$ | ![4-C$_4$H$_9$(t)-5-NHCOCHO-C$_{12}$H$_{25}$ benzodioxole] | H |
| I-44 | —NH$_2$ | | Cl |
| I-45 | —NH—C$_6$H$_5$ | ![2-Cl-NHCOCHO-C$_{12}$H$_{25}$ phenyl] | —S—C$_6$H$_4$—OCH$_3$ |
| I-46 | —NHCO—C$_6$H$_5$ | ![3-C$_{15}$H$_{31}$ phenyl] | Cl |
| I-47 | —C$_6$H$_5$ | H | H |

Compounds represented by Formula II $$\text{Formula II structure with } R_1, R_2, X$$

| No. | $R_1$ | $R_2$ | X |
|---|---|---|---|
| II-1 | —CH$_3$ | H | H |
| II-2 | —C$_6$H$_5$ | —NHCOCH$_3$ | H |
| II-3 | —C$_{15}$H$_{31}$ | H | Cl |

-continued

| No. | R₁ | R₂ | X |
|---|---|---|---|
| II-4 | 4-(OC₁₂H₂₅)-phenyl-NHSO₂− | −NHCOCH₃ | H |
| II-5 | −CH(CH₃)(CH₂)₂NHCO(CH₂)₃O−(3-C₁₅H₃₁-phenyl) | −NHSO₂−phenyl | Cl |
| II-6 | −SCH₂−(4-NHCOCH(C₆H₁₃)-phenyl with 2-C₅H₁₁(t), 4-C₅H₁₁(t)) | H | Cl |
| II-7 | 3-(NHSO₂C₁₁H₂₃)-phenyl-NH− | −NHCONH−(4-CN-phenyl) | H |
| II-8 | 4-(OC₁₈H₃₇)-phenyl-NH− | H | Br |
| II-9 | −OC₁₂H₂₅ | −OCH₃ | Cl |
| II-10 | 3-(C₁₁H₂₃)-phenyl-NHCONH− | −OCH₃ | H |
| II-11 | −CONHC₁₂H₂₅ | H | Cl |
| II-12 | −SO₂N(C₈H₁₇)₂ | H | H |

-continued

| No. | R₁ | R₂ | X |
|---|---|---|---|
| II-13 | —COCH₂—C₆H₄—NHCOC₁₃H₂₇ | H | Cl |
| II-14 | —C₆H₅ | —NH₂ | H |
| II-15 | H | —OC₁₂H₂₅ | H |
| II-16 | —CH(CH₃)₂ | —NHCOC₁₃H₂₇ | Cl |
| II-17 | —C₆H₄(OCH₃) (o-) | —NHCOCHO(C₂H₅)—C₆H₃(C₅H₁₁(t))(C₅H₁₁(t)) | Cl |
| II-18 | —SO₂CH₂—C₆H₄—OC₂H₅ | —NHCOCH₂O—C₆H₃(C₅H₁₁(t))(C₅H₁₁(t)) | H |
| II-19 | —C₁₂H₂₅ | H | H |
| II-20 | —COOC₁₈H₃₇ | H | Cl |
| II-21 | —C₆H₄—NHSO₂C₂₁H₂₅ (o-) | Cl | Cl |
| II-22 | —SCH₃ | —NHSO₂C₁₂H₂₅ | H |
| II-23 | —C₆H₃(OC₁₂H₂₅)(CH₃) | —NHCOC₁₃H₂₇ | H |

-continued

| No. | R₁ | R₂ | X |
|---|---|---|---|
| II-24 | —NHSO₂—C₆H₄—Cl | —OCH₃ | H |
| II-25 | CH₃—C(CH₃)(CH₃)—CH₂SO₂C₁₈H₃₇ | —NHCONHCH₃ | Cl |
| II-26 | —C₁₆H₃₃ | H | 4-CH₃-C₆H₄-O— |
| II-27 | —NHC₆H₅ | Br | H |
| II-28 | 2-CH₃-C₆H₄(NHCOC₁₁H₂₃)— | —CH₃ | H |
| II-29 | 4-OC₁₁H₂₃-C₆H₄—SO₂NH— | H | H |
| II-30 | —C₄H₉(t) | Cl | H |
| II-31 | cyclohexyl | —NHSO₂C₁₆H₃₃ | Cl |
| II-32 | —CH₃ | —NHCOCH(C₈H₁₇)-O-C₆H₃(C₅H₁₁(t))(C₅H₁₁(t)) | Cl |

-continued

| No. | R₁ | R₂ | X |
|---|---|---|---|
| II-33 | $-C(CH_3)_2(CH_2)_2O$-C₆H₄-C₁₅H₃₁ | $-NHCOC_4H_9$ | H |
| II-34 | $-C(CH_3)_3$ | $-NHSO_2$-C₆H₄-OC₁₂H₂₅ | Cl |
| II-35 | $-C_{16}H_{33}$ | $-NHCOCHO(C_{10}H_{21})$-C₆H₃(Cl)-SO₂-C₆H₃(Cl)-OH | H |
| II-36 | 5-methylfuran-2-yl | $-NHCOCHO(C_{12}H_{25})$-benzodioxole-C₄H₉(t) | H |
| II-37 | $-NHCOCH_3$ | $-NHSO_2$-C₆H₄-C₁₈H₃₇ | Cl |
| II-38 | $-NHC_6H_5$ | $-NHCOCHO(C_{12}H_{25})$-C₆H₄-Cl | Cl, -S-C₆H₄-OCH₃ |
| II-39 | $-OC_2H_5$ | $-NHCO(CH_2)_3O$-C₆H₄-C₁₅H₃₁ | Cl |
| II-40 | $-C_6H_5$ | $-NHCOC_{11}H_{23}$ | H |

-continued

| No. | R₁ | R₂ | X |
|---|---|---|---|
| II-41 | $-SO_2N(C_3H_7)_2$ | $-NHSO_2$-(phenyl with $C_8H_{17}$ and $OC_4H_9$) | H |
| II-42 | (1-methylpyrazol-yl) | $-NHCO(CH_2)_3O$-(phenyl-$C_{15}H_{31}$) | Cl |
| II-43 | $-COOCH_3$ | $-NHSO_2C_{16}H_{33}$ | (pyrazol-1-yl) |
| II-44 | (2-thienyl-methyl, $-CH_2$-thiophene) | $-NHCOCHO$-(phenyl with $C_5H_{11}(t)$ and $C_5H_{11}(t)$)-$C_{11}H_{23}$ | H |
| II-45 | $-CH_2$-(phenyl-$NHCOC_{18}H_{37}$) | $-NHCOC_2H_5$ | Cl |
| II-46 | $-CH_3$ | $-NHSO_2$-(phenyl with $C_8H_{17}$ and $OC_4H_9$) | Cl |
| II-47 | $-C_6H_5$ | $-NHCOCHO$-(methylenedioxyphenyl with $C_4H_9(t)$)-$C_3H_7(i)$ | H |

-continued

| No. | R₁ | R₂ | X |
|---|---|---|---|
| II-48 | (2-furyl) | —NHCOCH(C₁₀H₂₁)—[2,4-di-t-C₅H₁₁-phenyl] | —N=N—[2-(COOC₂H₅)phenyl] |
| II-49 | —NHCOCH₃ | —NHSO₂—[4-C₈H₁₇, 2-OC₄H₉-phenyl] | [4-methoxyphenyl-N=N-8-NHCOCH₃-1-OH-2-(naphthalene with KO₃S at 3, SO₃K at 6)] |
| II-50 | —C(CH₃)₃ | —NHSO₂—[4-OC₁₂H₂₅-phenyl] | [4-methoxyphenyl-N=N-8-NHCOCH₃-1-OH-2-(naphthalene with KO₃S at 3, SO₃K at 6)] |

The above-described couplers (hereinafter referred to as the couplers of the invention) can be synthesized in the synthesizing processes described in, for example, Pharmazie, 1976, 31(8), pp.546–548: Journal of Heterocyclic Chemistry, 1976, 13(6), pp.1305–1308: ibid., 1980, 17(7), pp.1435–1439: Journal of Organic Chemistry: and East German Patent No. 123,468.

The couplers of the invention can be used in an amount within the range of, usually, $1 \times 10^{-3}$ mols to 1 mol and, preferably, $1 \times 10^{-2}$ mols to $8 \times 10^{-1}$ mols per mol of silver halides used.

The couplers of the invention can be used together with the other kinds of cyan couplers.

The couplers of the invention can be similarly applied with the processes and techniques applicable to ordinary dye-forming couplers.

For preparing the photographic light-sensitive materials of the invention, it is preferable to apply a color light-sensitive material preparation process in which the foregoing couplers are compounded in silver halide emulsions and the emulsions are coated over a support, respectively. The photographic light-sensitive materials of the invention can be used as, for example, color photographic light-sensitive materials such as color-negative and color-positive films and color print papers.

The light-sensitive materials of the invention, including color print papers, may be either of the monocolor type or of the multicolor type. In the case of multicolor light-sensitive materials, the couplers of the invention can be added into any layers and, usually, into a red-sensitive silver halide emulsion layer. Such multicolor light-sensitive materials have dye-image forming component units respectively sensitive to the three primary color spectral regions. Each component unit may be comprised of a single layer or a multilayered emulsion layer which is sensitive to a certain spectral region. In light-sensitive materials, the component layers, including the image forming component unit layers, may be arranged in various order known in the photographic industry.

Typically, a multicolor light-sensitive material is comprised of a support bearing thereon a cyan dye image forming component unit comprising a red-sensitive silver halide emulsion layer containing the cyan coupler of the invention, a magenta dye image forming component unit comprising a green-sensitive silver halide emulsion layer containing a magenta coupler, and a yellow dye image forming component unit comprising a blue-sensitive silver halide emulsion layer containing an yellow coupler.

Such light-sensitive materials may have additional layers such as a filter layer, an interlayer, a protective layer and a subbing layer. The coupler of the invention can be contained in an emulsion in any conventionally known processes. For example, the couplers of the invention independently or in combination with the other couplers are dissolved in a high-boiling organic solvent having a boiling point of not lower than 175° C. such as tricresyl phosphate or dibutyl phthalate, or a low-boiling solvent such as butyl acetate or butyl propionate, independently or, if required, in the mixed solvent thereof. Then, the solution is mixed with an aqueous gelatin solution containing a surfactant. Next, the mixed solution is emulsified by means of a high-speed rotary mixer or a colloid-mill. Thus, the emulsion is added into a silver halide emulsion.

The compositions of each silver halide emulsion preferably applicable to the light-sensitive materials of the invention include silver chloride, silver chlorobromide and silver chloroiodobromide. The mixtures or combinations of silver chloride and silver bromide, for example, may be included therein. To be more concrete, in the case of applying a silver halide emulsion to a color print paper, a particularly rapid developability is required. It is, therefore, preferable to contain chlorine atoms as the halogen composition of silver halide and, particularly preferable to be silver chloride, silver chlorobromide or silver chloroiodobromide each containing silver chloride of at least 1%.

Such silver halide emulsions may be chemically sensitized in an ordinary process, and they may also be optically sensitized to any desired wavelength region.

For the purposes of preventing a light-sensitive material from fogging and/or keeping its photographic characteristics stable in the course of preparing, storing or processing it, the compounds may be added into its silver halide emulsion, as an antifoggant or a stabilizer known in the photographic industry.

It is also permitted to apply the color light-sensitive materials of the invention with an anti-color foggant, a dye-image stabilizer, a UV absorbent, an antistatic agent, a matting agent, and a surfactant, each usually used in light-sensitive materials.

For the details of such additives, it may be referred to, for example, Research Disclosure, vol 176, pp.22–31, December, 1978.

With the color photographic light-sensitive materials of the invention, images can be formed by carrying out the color developments known in the art.

The color photographic light-sensitive materials relating to the invention contain a color developing agent either as itself or as its precursor in the hydrophilic colloidal layers thereof so that they can be processed in an alkaline activation bath.

The color photographic light-sensitive materials relating to the invention are bleached and fixed after they were developed. The bleaching step may be carried out at the same time when the fixing step is made.

After completing the fixing step, a washing step is usually carried out. And, a stabilizing step may be carried out in place of the washing step, and the both steps may also be carried out in combination.

EXAMPLES

Example-1

On a paper support laminated on the both sides with polyethylene, the following each layer was coated in order from the support side, so that red-sensitive color liqht-sensitive material sample 1 was prepared. Wherein, the amounts of compounds added therein are expressed in terms of an amount per sq. meter, unless otherwise expressly indicated, provided that the amounts of silver halide used are expressed in terms of the silver contents.

Layer 1: An emulsion layer

This layer was a red-sensitive emulsion layer comprising 1.2 g of gelatin, 0.30 g of a red-sensitive silver chlorobromide emulsion containing silver chloride of 96 mol %, and $9.1 \times 10^{-4}$ mols of comparative cyan coupler A dissolved in 1.35 g of dioctyl phosphate.

Layer 2: A protective layer

This layer contained 0.50 g of gelatin, and sodium salt of 2,4-dichloro-6-hydroxy-s-triazine was also added as a hardener so as to make an amount of 0.017 g per g of gelatin used.

Next, Samples 2 through 15 each relating to the invention were prepared in quite the same manner as in Sample 1, except that Comparative coupler A was replaced by each of the couplers shown in Table-1, which was added in the same mol as that of Comparative coupler A.

The resulting Samples 1 through 15 were exposed wedge wise to light in an ordinary method and were then processed in the following steps.

| Processing steps | | |
|---|---|---|
| Color developing | 38° C. | 3 min. 30 sec. |
| Bleach-fixing | 38° C. | 1 min. 30 sec. |
| Stabilizing or washing | 25° C. to 30° C. | 3 min. |
| Drying | 75° C. to 80° C. | 2 min. |

The compositions of the processing solutions used in the above processing steps were as follows:

| Color Developer | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid, TPPS | 2.5 g |
| 3-methyl-4-amino-N-ethyl-N-(β-methane-sulfonamidoethyl)aniline sulfate | 5.5 g |
| Fluorescent brightening agent, 4,4'-diaminostilbenedisulfonic acid derivative | 1.0 g |
| Potassium hydroxide | 2.0 g |
| Add water to make in total | 1 liter |
| Adjust pH to be | pH 10.20 |
| Bleach Fixer | |
| Ferric ammonium ethylenediamine-tetraacetate dihydride | 60 g |
| Ethylenediaminetetraacetic acid | 3 g |
| Ammonium thiosulfate, in an aqueous 70% solution | 100 ml |
| Ammonium sulfite, in an aqueous 40% solution | 27.5 ml |
| Adjust pH with potassium carbonate or glacial acetic acid to be | pH 7.1 |
| Add water to make in total | 1 liter |
| Stabilizer | |
| 5-chloro-2-methyl-4-isothiazoline-3-one | 1.0 g |
| Ethylene glycol | 10 g |
| Add water to make | 1 liter |

With thus processed Samples 1 through 15, the densities thereof were measured with a densitometer Model KD-7 manufactured by Konica Corporation and, after allowing them to stand for 14 days under a high temperature and high humidity atmosphere, 60° C., 80% RH, the heat resistance and moisture resistance of the dye images resulted from each of the samples were inspected.

After each sample was exposed to a Xenon Fade-o-meter for 10 days, the density thereof was measured and the light fastness was inspected. The results thereof are shown in Table-1. In the table, the heat resistance, moisture resistance and light fastness of each dye image are expressed in terms of a percentage of the residual dyes to the initial density set at 1.0, which was obtained after tested the heat resistance, moisture resistance and light fastness.

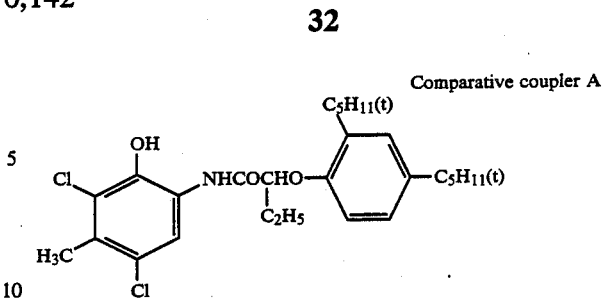

Comparative coupler A

TABLE-1

| Sample No. | Coupler used | Dye residual Percentage (%) | |
|---|---|---|---|
| | | Heat resistance Moisture resistance | Light fastness |
| 1 | Comparative coupler A | 61 | 82 |
| 2 | Exemplified compound I-3 | 88 | 84 |
| 3 | Exemplified compound I-8 | 90 | 83 |
| 4 | Exemplified Compound I-10 | 90 | 82 |
| 5 | Exemplified compound I-16 | 88 | 85 |
| 6 | Exemplified compound I-23 | 90 | 86 |
| 7 | Exemplified compound I-39 | 86 | 80 |
| 8 | Exemplified compound I-41 | 84 | 82 |
| 9 | Exemplified compound II-4 | 89 | 81 |
| 10 | Exemplified compound II-7 | 86 | 84 |
| 11 | Exemplified compound II-8 | 89 | 82 |
| 12 | Exemplified compound II-16 | 89 | 80 |
| 13 | Exemplified compound II-18 | 91 | 84 |
| 14 | Exemplified compound II-22 | 91 | 81 |
| 15 | Exemplified compound II-25 | 90 | 82 |

As is obvious from the results shown in Table-1, it is found that every sample of the invention were high in dye residual percentage, and excellent in heat resistance, moisture resistance and light fastness, as compared to the sample used therein the comparative coupler.

EXAMPLE-2

On a subbed triacetate film support, the following each layer was coated in order from the support side, so that a red-sensitive color light-sensitive material named herein sample 16 was prepared. Wherein, the amounts of compounds added therein are expressed in terms of an amount per sq. meter, unless otherwise expressly indicated, provided that the amounts of silver halide used are expressed in terms of the silver contents.

Layer 1: An emulsion layer

This layer was a red-sensitive emulsion layer comprising 1.4 g of gelatin, 1.5 g of a red-sensitive silver iodobromide emulsion containing silver iodide of 4 mol %, and $8.0 \times 10^{-4}$ mols of comparative cyan coupler B dissolved in 1.1 g of tricresyl phosphate.

Layer 2: A protective layer

This layer contained 1.5 g of gelatin, and sodium salt of 2,4-dichloro-6-hydroxy-s-triazine was also added as a hardener so as to make an amount of 0.017 g per g of gelatin used.

Next, Samples 17 through 30 each relating to the invention were prepared in quite the same manner as in Sample 16, except that Comparative coupler B was replaced by each of the couplers shown in Table-2, which was added in the same mol as that of Comparative coupler B.

The resulting film samples were each exposed wedge-wise to light in an ordinary method and were then color processed in the following color processing steps.

Comparative coupler B

OH
  |
  [naphthalene]—CONH(CH$_2$)$_4$—O—[benzene]—C$_5$H$_{11}$(t)
                                      |
                                      C$_5$H$_{11}$(t)

Processing steps (At a processing temperature of 38° C.)

|  | Processing time |
|---|---|
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |
| Drying |  |

The compositions of the processing solutions used in the above processing steps were as follows:

| Color developer | |
|---|---|
| 4-amino-3-methyl-N-ethyl-N-(β-hydroxyethyl)aniline sulfate | 4.75 g |
| Sodium sulfite, anhydride | 4.25 g |
| Hydroxyamine ½ sulfate | 2.0 g |
| Potassium carbonate, anhydride | 37.5 g |
| Sodium bromide | 1.3 g |
| Trisodium nitrilotriacetate, monohydrate | 2.5 g |
| Potassium hydroxide | 1.0 g |
| Add water to make | 1 liter |
| Adjust pH with sodium hydroxide to be | pH 10.6 |
| Bleaching solution | |
| Ferric ammonium ethylenediaminetetraacetate | 100.0 g |
| Diammonium ethylenediaminetetraacetate | 10.0 g |
| Ammonium bromide | 150.0 g |
| Glacial acetic acid | 10.0 g |
| Add water to make | 1 liter |
| Adjust pH with aqueous ammonia to be | pH 6.0 |
| Fixer | |
| Ammonium thiosulfate | 175.0 g |
| Sodium sulfite, anhydride | 8.6 g |
| Sodium metasulfite | 2.3 g |
| Add water to make | 1 liter |
| Adjust pH with acetic acid to be | pH 6.0 |
| Stabilizer | |
| Formalin, in an aqueous 37% solution | 1.5 ml |
| Konidux, manufactured by Konica Corp. | 7.5 ml |
| Add water to make | 1 liter |

With thus processed samples 16 through 30, the transmission densities thereof were measured with a densitometer Model KD-7R manufactured by Konica Corp. and the samples were then allowed to stand for 14 days under a high temperature and high humidity atmosphere at 60° C. and 80% RH, so that the heat resistance and moisture resistance of the resulting dye images were inspected.

And, the light fastness of each sample was inspected after they were exposed to a Xenon Fade-o-meter for 10 days. The results thereof are shown in Table-2. Wherein the heat resistance, moisture resistance and light fastness of each dye image are expressed in terms of a percentage of the residual dyes to the initial density set at 1.0, which was obtained after tested the heat resistance, moisture resistance and light fastness.

TABLE-2

| Sample No. | Coupler used | Dye residual percentage (%) Heat resistance Moisture resistance | Light fastness |
|---|---|---|---|
| 16 | Comparative coupler B | 72 | 81 |
| 17 | Exemplified compound I-7 | 89 | 83 |
| 18 | Exemplified compound I-9 | 91 | 84 |
| 19 | Exemplified compound I-19 | 87 | 81 |
| 20 | Exemplified compound I-28 | 88 | 80 |
| 21 | Exemplified compound I-32 | 90 | 85 |
| 22 | Exemplified compound I-35 | 90 | 84 |
| 23 | Exemplified compound I-46 | 84 | 80 |
| 24 | Exemplified compound II-17 | 83 | 81 |
| 25 | Exemplified compound II-23 | 87 | 82 |
| 26 | Exemplified compound II-32 | 89 | 83 |
| 27 | Exemplified compound II-34 | 85 | 80 |
| 28 | Exemplified compound II-39 | 90 | 83 |
| 29 | Exemplified compound II-40 | 86 | 79 |
| 30 | Exemplified compound II-42 | 84 | 81 |

As is obvious from the results shown in Table-2, it is found that every sample of the invention were high in dye residual percentage, and excellent in heat resistance, moisture resistance and light fastness, as compared to the sample used therein the comparative coupler.

EXAMPLE-3

On a triacetyl cellulose film support, the following each layer was coated in order from the support side, so that red-sensitive color reversal light-sensitive materials containing the couplers shown in Table-3, named herein Samples 31 through 41, were prepared, respectively.

Layer 1: An emulsion layer

This layer was a red-sensitive emulsion layer comprising 1.4 g of gelatin, 0.5 g of a red-sensitive silver chloro bromide emulsion containing silver chloride of 96 mol %, and $9.1 \times 10^{-4}$ moles of the coupler shown in Table-3 dissolved in 1.5 g of dibutyl phtharate.

Layer 2: A protective layer

This layer contained 0.5 g of gelatin, and sodium salt of 2,4-dichloro-6-hydroxy-s-triazine was also added as a hardener so as to make an amount of 0.017 g per g of gelatin used.

The resulting samples were each exposed wedgewise to light in an ordinary method and were then processed in the following color processing steps.

Reversal processing steps

| Step | Time | Temperature |
|---|---|---|
| First developing | 6 min. | 38° C. |
| Washing | 2 min. | 38° C. |
| Reversing | 2 min. | 38° C. |
| Color developing | 6 min. | 38° C. |
| Moderation | 2 min. | 38° C. |
| Bleaching | 6 min. | 38° C. |
| Fixing | 4 min. | 38° C. |
| Washing | 4 min. | 38° C. |
| Stabilizing | 1 min. | 38° C. |
| Drying |  | At ordinary temperature |

The following compositions of the processing solutions were used.

| First developer | |
|---|---|
| Sodium tetrapolyphosphate | 2 g |
| Sodium sulfite | 20 g |

| | |
|---|---|
| Hydroquinone monosulfonate | 30 g |
| Sodium carbonate, monohydrate | 30 g |
| 1-phenyl-4-methyl-4-hydroxymethyl-3-pyrazolidone | 2 g |
| Potassium bromide | 2.5 g |
| Potassium thiocyanate | 1.2 g |
| Potassium iodide, in an aqueous 0.1% solution | 2 ml |
| Add water to make | 1000 ml |
| Reversing solution | |
| Hexasodium nitrilotrimethylenephosphonate | 3 g |
| Stannous chloride, dihydrate | 1 g |
| p-aminophenol | 0.1 g |
| Sodium hydroxide | 5 g |
| Glacial acid | 15 ml |
| Add water to make | 1000 ml |
| Color developer | |
| Sodium tetrapolyphosphonate | 2 g |
| Sodium sulfite | 7 g |
| Tertiary sodium phosphate, dodecahydrate | 36 g |
| Potassium bromide | 1 g |
| Potassium iodide, in an aqueous 0.1% solution | 90 ml |
| Sodium hydroxide | 3 g |
| Citrazinic acid | 1.5 g |
| N-ethyl-N-(β-methanesulfonamidoethyl)--3-methyl-4-aminoaniline sulfate | 11 g |
| Ethylenediamine | 3 g |
| Add water to make | 1000 ml |
| Moderating solution | |
| Sodium sulfite | 12 g |
| Sodium ethylenediaminetetraacetate, dihydrate | 8 g |
| Thioglycerol | 0.4 ml |
| Glacial acetic acid | 3 ml |
| Add water to make | 1000 ml |
| Bleaching solution | |
| Sodium ethylenediaminetetracetate, dihydrate | 2.0 g |
| Ferric ammonium ethylenediamine-tetraacetate, dihydrate | 120.0 g |
| Potassium bromide | 100.0 g |
| Add water to make | 1000 ml |
| Fixing solution | |
| Ammonium thiosulfate | 80.0 g |
| Sodium sulfite | 5.0 g |
| Sodium bisulfite | 5.0 g |
| Add water to make | 1000 ml |
| Stabilizer | |
| Formalin (37 wt %) | 5.0 ml |
| Konidux, manufactured by Konica Corp. | 5.0 ml |
| Add water to make | 1000 ml |

With this processed samples, the heat resistance, moisture resistance and light fastness of the resulting dye images were inspected in the same manner as in Example-2. The results thereof are shown in Table-3.

TABLE-3

| Sample No. | Coupler used | Dye residual percentage (%) Heat resistance Moisture resistance | Light fastness |
|---|---|---|---|
| 31 | Comparative coupler A | 63 | 84 |
| 32 | Exemplified compound I-15 | 89 | 83 |
| 33 | Exemplified compound I-17 | 92 | 82 |
| 34 | Exemplified compound I-20 | 93 | 82 |
| 35 | Exemplified compound I-22 | 89 | 85 |
| 36 | Exemplified compound I-25 | 90 | 84 |
| 37 | Exemplified compound II-43 | 90 | 81 |
| 38 | Exemplified compound II-44 | 89 | 83 |
| 39 | Exemplified compound II-45 | 89 | 84 |
| 40 | Exemplified compound II-46 | 90 | 82 |
| 41 | Exemplified compound II-47 | 91 | 80 |

As is obvious from the results shown in Table-3, it is found that every sample of the invention were high in dye residual percentage, and excellent in heat resistance, moisture resistance and light fastness, as compared to the sample used therein the comparative coupler.

What is claimed is:

1. A silver halide photographic light-sensitive material containing a coupler represented by the following formula I or II:

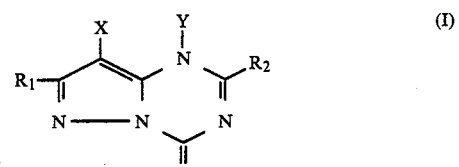

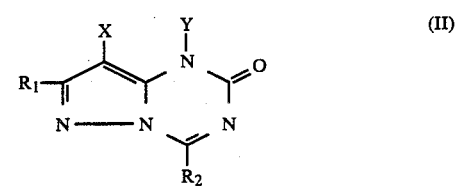

wherein, $R_1$, $R_2$ and Y are independently a hydrogen atom or a substituent; Z is an oxygen atom or a sulfur atom, X is a hydrogen atom or a substituent capable of splitting off upon reaction with the oxidation product of a color developing agent.

2. The material of claim 1, wherein said $R_1$ and $R_2$ are each a hydrogen atom, an alkyl group, an aryl group, an anilino group, an acylamino group, a sulfonamido group, an alkylthio group, an arylthio group, an alkenyl group, a cycloalkyl group, a halogen atom, a cycloalkenyl group, an alkinyl group, a heterocyclic group, a sulfonyl group, a sulfinyl group, a phosphonyl group, an acyl group, a carbamoyl group, a sulfamoyl group, a cyano group, an alkoxy group, a sulfonyloxy group, an aryloxy group, a heterocyclic-oxy group, a siloxy group, an acyloxy group, a carbamoyloxy group, an amino group, an alkylamino group, an imido group, a ureido group, a sulfamoylamino group, an alkoxycarbamoylamino group, an aryloxycarbamoylamino group, an alkoxycarbonyl group, an aryloxycarbonyl group, a heterocyclic-thio group, a thioureido group, a carboxy group, a hydroxy group, a mercapto group, a nitro group, a sulfonic acid group, a residue of spiro compound or a residue of bridged hydrocarbon compound.

3. The material of claim 2, wherein said $R_1$ and $R_2$ are each an alkyl group, an aryl group, an anilino group, an acylamino group, a sulfonamido group, an alkylthio group, an arylthio group, an alkenyl group or a cycloalkyl group.

4. The material of claim 1, wherein said X is a hydrogen atom, a halogen atom, an alkyl group, an alkoxy group, an aryloxy group, a heterocyclic-oxy group, an acyloxy group, a sulfonyloxy group, an alkoxycarbonyloxy group, an aryloxycarbonyl group, an alkoxyalyloxy group, an alkoxyoxalyloxy group, an alkylthio group, an arylthio group, a heterocyclicthio group, an alkyloxythiocarbonylthio group, an acylamino group, a sulfonamido group, a nitrogen-containing heterocyclic group bonding at a N atom thereof to the coupler, an alkyloxycarbonylamino group, a carboxy group or a group represented by the following Formula Ia for Formula I and Formula IIa for Formula II:

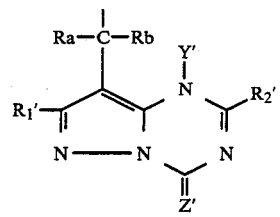 (Ia)

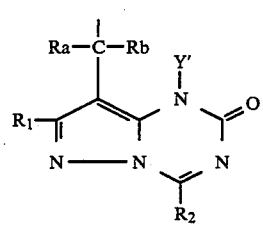 (IIa)

wherein $R_1'$, $R_2'$, $Y'$ and $Z'$ are the same as $R_1$, $R_2$, $Y$ and $Z$ defined in Formulas I and II, respectively.

5. The material of claim 4, wherein said X is a hydrogen atom or a halogen atom.

6. The material of claim 5, wherein said X is a hydrogen atom or a chlorine atom.

7. The material of claim 1, wherein said Y is a hydrogen atom.

8. The material of claim 1, wherein said Z is an oxygen atom.

9. The material of claim 1, wherein said coupler is represented by the following formula Ib:

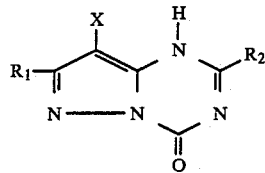 (Ib)

wherein $R_1$, $R_2$ and X are the same as defined in formula I.

10. The material of claim 1, wherein said coupler is represented by the following formula IIb:

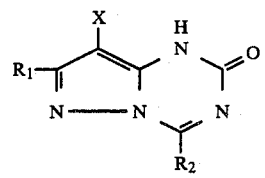 (IIb)

wherein $R_1$, $R_2$ and X are the same as defined as in formula II.

11. The material of claim 1, wherein said coupler is contained in a silver halide emulsion layer of said silver halide light-sensitive material.

12. The material of claim 11, wherein said silver halide emulsion layer contains said compound in an amount of from $1 \times 10^{-3}$ to 1 mol per mole of silver contained in said silver halide emulsion layer.

13. The material of claim 12, wherein said silver halide emulsion layer contains said compound in an amount of from $1 \times 10^{-2}$ to $8 \times 10^{-1}$ mole per mole of silver contained in said silver halide emulsion layer.

* * * * *